United States Patent [19]

Hendrix

[11] Patent Number: 5,068,464

[45] Date of Patent: Nov. 26, 1991

[54] PROCESS FOR THE OXIDATION OF HYDROCARBONS UTILIZING PARTITIONING OF OXIDIZING GAS

[75] Inventor: David C. Hendrix, Lake Jackson, Tex.

[73] Assignee: BASF Corporation, Wyandotte, Mich.

[21] Appl. No.: 199,844

[22] Filed: May 26, 1988

[51] Int. Cl.$^5$ .............................................. C07C 45/33
[52] U.S. Cl. .................................. 568/357; 568/360; 568/836; 568/399
[58] Field of Search ................ 568/357, 360, 836, 399

[56] References Cited

U.S. PATENT DOCUMENTS

| 3,564,058 | 2/1971 | Lang et al. | 568/360 |
| 3,957,876 | 5/1976 | Rapoport et al. | 568/836 |
| 4,491,674 | 1/1985 | Rieber et al. | 568/836 |
| 4,587,363 | 5/1986 | Hartig et al. | 568/836 |
| 4,735,741 | 4/1988 | Grosskinsky et al. | 568/357 |

OTHER PUBLICATIONS

Perry et al., "Chemical Engineers' Handbook", Fifth Edn. pp. 14—2-14—4 (1979).

*Primary Examiner*—James H. Reamer

[57] ABSTRACT

A continuous process for the partial oxidation of hydrocarbons is disclosed wherein the oxidizing gas is partitioned into the hydrocarbon by means of countercurrent flow of an aqueous solution of oxygen prepared in a separate vessel, thus avoiding direct contact of hydrocarbon and oxidizing gas.

19 Claims, 2 Drawing Sheets

PROCESS FOR THE OXIDATION OF HYDROCARBONS UTILIZING PARTITIONING OF OXIDIZING GAS

BACKGROUND OF THE INVENTION

1. Field of the Invention

The subject invention relates to an improved process for the controlled oxidation of hydrocarbons. More particularly, the subject invention relates to the partitioning of oxygen from an aqueous solution into the hydrocarbon to be oxidized, and recovery of excess oxygen from oxidized hydrocarbon.

2. Description of the Related Art

The controlled oxidation of hydrocarbons, in particular aliphatic and cycloaliphatic hydrocarbons, represents an important industrial means for the preparation of many oxygenated organic compounds including alcohols, aldehydes, ketones, and carboxylic acids, to name but a few. For example, cyclohexane is useful as a feedstock to produce a wide range of products through partial oxidation including cyclohexanol, cyclohexanone, adipic acid, and e-hydroxycaproic acid. These products may then serve as intermediates in the preparation of such widely varied products as hexanediol and caprolactam.

Other hydrocarbons which are frequently oxidized to form oxygenated products include butane, hexane, cyclohexene, benzene, and naphthalene. It is fair to say that oxygenation processes involving these and other hydrocarbons produce a fair proportion of the commodity organic chemicals in the marketplace.

Unfortunately, the controlled oxidation of hydrocarbons, which generally takes place at elevated temperatures, presents severe safety problems. The direct introduction of oxygen, either in its pure state, as atmospheric oxygen, or as enriched atmospheric oxygen, into any hot, flammable liquid creates the danger of fire or explosion. This is especially true when oxidation takes place in the vapor phase or where the apparatus utilized allows oxygen containing hydrocarbon vapors to accumulate in the reactor head space. In the latter case, pure oxygen represents a greater danger than air, because the range of explosive limits is substantially wider. The fact that highly unstable peroxides and hydroperoxides often comprise a significant proportion of the oxidate enhances the dangers inherent in these processes.

In conventional oxidation, air is admitted to the bottom of the reactors as fine bubbles, and the headspace is carefully monitered for the presence of unreacted oxygen. In European application EP-A-0199 339, pure oxygen is used, and direct initial contact between oxygen and hydrocarbon is avoided by admitting oxygen in the form of a fine dispersion into a lower aqueous layer. The hydrocarbon to be oxidized is admitted into the oxygen solutioning vessel above the aqueous layer. However, this process has a disadvantage in that, although initial contact between oxygen and hydrocarbon is prevented by careful control pure gaseous oxygen is still physically present in the solutioning vessel and thus a greater danger of explosion exists.

SUMMARY OF THE INVENTION

It has been discovered that many of the dangers associated with the direct introduction of oxidizing gases such as oxygen into hydrocarbons can be eliminated by first dissolving the oxidizing gas into water in a separate vessel and then partitioning the gas into the hydrocarbon to be oxidized by contacting the aqueous oxygen solution with the liquid hydrocarbon. Under these conditions, oxygen is transferred into the hydrocarbon under controlled conditions during which gaseous oxygen is substantially absent, which greatly enhances the safety of the overall oxidation process.

BRIEF DESCRIPTION OF THE DRAWINGS

FIG. 2 depicts a means for removing oxygen in excess over that consumed during oxidation by reverse partitioning.

DESCRIPTION OF THE PREFERRED EMBODIMENTS

Figure 1:
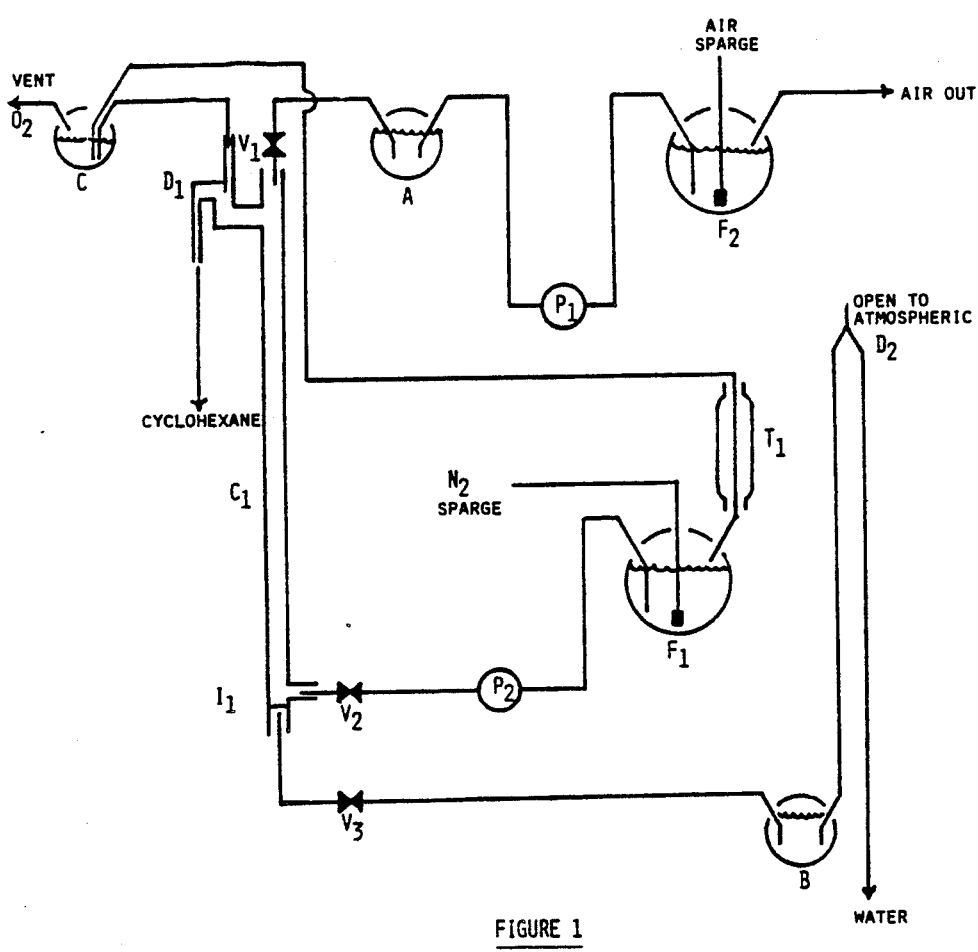
FIG. 1 represents a laboratory apparatus which is useful to demonstrate the transfer of oxygen into liquid hydrocarbon from an aqueous oxygen solution.

The oxidation of hydrocarbons is a well known and widely practiced industrial process. Description of the oxidation process, the types of hydrocarbon substrates, the catalysts used, and other details may be found, for example, in *The Oxidation of Cyclohexane*, Berezin, et. al., Pergamon Press, New York, ©1966; *The Oxidation of Hydrocarbons in the Liquid Phase*, Emanuel, Ed., Pergamon Press, the MacMilan Co., New York, ©1965; and many U.S. patents, including U.S. Pat. Nos. 4,322,558; 3,933,930; 3,923,895; 3,937,735; 3,991,099; 3,681,447; 3,719,706; 3,761,517; 3,869,508; 3,965,164; 4,227,021; 4,263,453; 3,671,588; 3,932,513; 3,948,992; 3,987,115; 4,055,600; 4,098,817; 4,341,907; and 3,946,077.

In the process of the subject invention, a solution of oxygen in water is first prepared, preferably in continuous fashion. The oxygen from this aqueous solution is then transferred, or partitioned, into the hydrocarbon to be oxidized, by means of countercurrent partitioning or an equivalent means, preferably at ambient or below ambient temperatures. The hydrocarbon, containing dissolved oxygen, is then heated to the necessary oxidation temperature, and transferred to a reaction vessel. Following reaction, the products are separated from the unreacted hydrocarbon, which is recycled. Preferably, a major portion of the water used to provide the requisite oxygen is also recycled.

According to the process of the subject invention, an aqueous oxygen solution is prepared by dissolving air, oxygen enriched air, or oxygen into water under a pressure sufficient to dissolve the required quantity of oxygen under the prevailing process temperature. It is well known, at least as a first approximation, that the solubility of a gas in a liquid is directly proportional to the pressure of the gas. Thus at a pressure of 10 bar, oxygen has approximately ten times the solubility in water as at a pressure of one bar. Thus, from Gmelin's Handbook of Inorganic Chemistry, "Sauerstoff," 3d Ed., p. 461, the solubility of oxygen at one bar is approximately 0.04 g/l at 25° C. At ten bar, the solubility would be approximately 0.4 g/l, while at a pressure of 100 bar, the solubility would be approximately 4 g/l.

As the temperature rises, the solubility of oxygen in water decreases. Thus at 50° C., the solubility of atmospheric oxygen decreases from its value at 25° C. by about 30 percent. Thus during the process of dissolving oxygen in water, whether the oxygen is derived from air, oxygen enriched air, or from pure oxygen itself, the temperature should be maintained at as low a value as possible. Thus the water temperature may be maintained at ambient temperature, preferably below 70° C., and more preferably at room temperature (25° C.) or below. In the discussion which follows, use of the term oxygen shall mean oxygen in a state of relative purity, air, air enriched with oxygen, or mixtures containing oxygen and one or more gases which are inert under the process conditions.

In order to provide the preferred amount of oxygen in the hydrocarbon which is approximately 2-10 weight percent, the partial pressure of oxygen should be from about 5 to about 200 bar, preferably from 5 to about 100 bar, and more preferably from 7 to about 60 bar. The pressure necessary can be readily calculated, or may be experimentally determined based on established process parameters such as the maximum design operating pressure and the desired operating range of the equipment utilized. Oxygen pressure will depend on the desired concentration of oxygen in hydrocarbon, the relative amount of water to hydrocarbon, the number of transfer stages, and the equilibrium of oxygen between water and hydrocarbon. Based upon a theoretical four stage partitioning system, and a volume flow rate of water 7.2 times greater than that of cyclohexane a partial pressure of about 830 psia would be necessary to provide approximately 5 mole percent oxygen in cyclohexane, for example. Pressures required for other operating conditions are shown in Table I.

The dissolution of oxygen into the water may be accomplished by any convenient method. For example, oxygen may be bubbled through water which is maintained in a holding tank under pressure. Alternatively, oxygen may be introduced into the bottom of a column, preferably a packed column, with water being introduced at the top of the column, or water may be introduced as a spray into a column filled with oxygen. By utilizing such a countercurrent dissolution process, the use of large volumes of oxygen and water is economically feasible. Other means of dissolving oxygen in water will suggest themselves to those skilled in the art.

The water used to dissolve the oxygen may be fresh water, may be recycled water, or a combination of both. Preferably, most of the process water is recycled. The water may contain dissolved solids or organic materials which do not adversely affect either the oxygen dissolution or the oxidation reaction which will follow. The recycle water may also be obtained from a reverse partitioning stream of fresh or recycle water which is used to strip unreacted oxygen from the product oxygenated.

Basic materials, particularly strongly basic materials such as the alkali metal hydroxides should be avoided as these substances are known to slow down the oxidation reaction of the hydrocarbon. Furthermore, strongly basic aqueous solutions may cause precipitation of transition metal catalysts as their oxides, hydroxides, or hydrated oxides, thus not only eliminating their catalytic activity but causing potential fouling problems as well.

Aqueous solutions containing significant quantities of dissolved inorganic salts should be avoided, as such salts, when present in significant concentration, decrease the solubility of oxygen in the solution. If the recycle water in the process accumulates such substances over time, it may be necessary to add a separation stage to remove these substances, to adjust the quantity of water recycled, or to periodically restart the process using fresh water as the water source.

Preferably the water utilized should be neutral or slightly acidic, and may contain effective quantities of the particular oxidation catalyst when one is required. Such oxidation catalysts are well known to those skilled in the art, and are generally salts or complexes of metals, particularly transition metals or heavy metals such as cobalt, chromium, manganese, vanadium, aluminum, lead, tin, and copper. Numerous examples of such catalysts may be found in the references cited earlier. As many of these catalysts are water soluble to at least some degree, the same water which serves to provide the oxygen may also provide the catalyst supply to the hydrocarbon.

Partitioning of oxygen from the aqueous oxygen solution into the hydrocarbon to be oxidized is effected by contacting the two liquids, preferably in such a manner as to maximize the surface area of the liquid-liquid interface. Preferably, the two liquids are contacted in a countercurrent flow, packed column, at ambient temperature or below. Because of the generally greater solubility of oxygen in hydrocarbons, effective transfer of a substantial quantity of oxygen from the aqueous to the nonaqueous phase takes place readily, with the degree of transfer being limited by the partition coefficient of oxygen in the two liquids at the contact temperature. Furthermore, by circulating a greater volume of water than cyclohexane, the hydrocarbon oxygen concentration may be increased over that of the water. The term "substantial quantity" as used herein relates to a quantity which is a substantial fraction, i.e. at least 10 percent, of the quantity theoretically transferable.

Following partitioning of the oxygen into the hydrocarbon phase, the hydrocarbon is then heated to the desired oxidation temperature. When catalysts are utilized in the oxidation, they may be added prior to or subsequent to reaching the desired reaction temperature, or, as suggested previously, may be partitioned into the hydrocarbon from the aqueous phase. An inherent safety factor in the subject invention resides in the fact that, unlike its solubility in water, the solubility of oxygen in many hydrocarbons, particularly cyclohexane, increases with increasing temperature. Thus the solubility of oxygen at atmospheric pressure in cyclohexane is 12.3, 12.4, and 12.7 (x $10^4$) mole percent, respectfully, at 283.5° K. 297.6° K., and 313.1° K. This provides an additional safety factor, since a saturated solution of oxygen in hydrocarbon at room temperature will become unsaturated as the temperature is raised, and the oxygen will therefore be less likely to escape and form a vapor.

The oxidation process itself is entirely conventional. Following oxidation, the products are separated and purified in the conventional matter.

Hydrocarbons which are suitable for the process of the subject invention include benzene, toluene, and other light aromatic hydrocarbons, but in particular aliphatic hydrocarbons such as butane, pentane, hexane, isoctane, and the like, and most preferably cycloaliphatics such as cyclopentane, cyclopentene, cyclopentanol, cyclohexane, cyclohexene, cyclohexanol, methylcyclohexane, and dimethylcyclohexane. Most preferred is cyclohexane.

The subject invention will now be described with reference to the drawings and with reference to the example. This discussion should not be construed as limiting the scope of the invention in any way. Many useful variations of the claimed process will suggest themselves to one of ordinary skill in the art. All such variations are contemplated as being within the scope of the invention.

surement. Data taken over several runs is collected in Table I below.

TABLE I

| $H_2O$/Cyclohexane Flow Ratio[1] | Oxygen Pressure @ No. Theoretical Stages[2] | | | | | |
|---|---|---|---|---|---|---|
| | 1 Stage | 2 Stages | 3 Stages | 4 Stages | 5 Stages | 6 Stages |
| 3.6 | 3.6 | 2200 | 1660 | 1540 | 1500 | — |
| 6.0 | 6.0 | 1470 | 1130 | 1020 | 960 | 890 |
| 7.2 | 7.2 | 1320 | 1000 | 900 | 830 | 770 |
| 9.0 | 9.0 | 1180 | 900 | 790 | 740 | 660 |
| 11.2 | 11.2 | 1070 | 800 | 720 | 680 | — |
| 13.5 | 13.5 | 1010 | 760 | 680 | 640 | — |
| 21.6 | 21.6 | 850 | 680 | 640 | 640 | — |

[1]Flow Ratio in vol/vol.
[2]Oxygen partial pressure in psia.

TABLE II

| Example | Water[1] Flow | Cyclohexane Flow | Feed[2] $O_2$ | Exit $O_2$ | $O_2$ Transferred | Flow Ratio $H_2O$ Cyclohexane | Percent $O_2$ Transferred | $H_2O$/Cyclohexane[3] Contact Time |
|---|---|---|---|---|---|---|---|---|
| 1 | 5.27 | 0.84 | 8.52 | 6.10 | 2.42 | 6.27 | 28 | 3.06 |
| 2 | 5.30 | 0.82 | 8.72 | 6.08 | 2.64 | 6.46 | 30 | 3.09 |
| 3 | 5.70 | 0.84 | 8.65 | 5.95 | 2.70 | 6.78 | 31 | 2.92 |
| 4 | 5.75 | 0.69 | 8.28 | 5.80 | 2.48 | 8.33 | 30 | 3.00 |
| 5 | 5.85 | 0.69 | 8.32 | 6.19 | 2.13 | 8.47 | 26 | 3.06 |

[1]Water and cyclohexane flow rates in ml/minute
[2]All oxygen content in ppm. Feed $O_2$ measured from Vessel A, Exit $O_2$ from vessel B.
[3]Time of contact between falling water droplet and cyclohexane phase, sec.

EXAMPLE 1

The feasibility of partitioning oxygen into a hydrocarbon from aqueous solution was determined by the following experiment. With reference to FIG. 1, cyclohexane was introduced into vessel $F_1$ and sparged with nitrogen for 12 hours to remove any dissolved oxygen. Cyclohexane vapor was removed from the nitrogen outlet stream by trap $T_1$ and returned to the vessel. Distilled water was introduced into vessel $F_2$ and sparged with air for 12 hours to saturate it with atmospheric oxygen. Pressure was not increased beyond atmospheric except for the small back pressure created by the apparatus itself.

During the course of each run, water was pumped by Pump $P_1$ from vessel $F_2$ to holding vessel A and from there to the top of partitioning column $C_1$ through valve $V_1$. Partitioning column $C_1$ was an unpacked glass column of 25.0 cm length and c.a. 0.9 cm bore. At the same time, cyclohexane was pumped by pump $P_2$ to the partitioning column's cyclohexane inlet through valve $V_2$. Cyclohexane containing dissolved oxygen left the column at overflow device $D_1$. Water entered the column through a vertical section of ⅛″ tubing, fell downward through the cyclohexane in the form of droplets, without touching the column walls, and left the column through valve $V_3$ into holding vessel B. From there, it was removed from the apparatus at overflow $D_2$. The level of the water/cyclohexane interface I, was adjusted by adjusting the height of $D_2$. The flow rates of cyclohexane and water were measured periodically. The vapor space in vessels A and B was maintained at a minimum. Vapor of any kind was carefully excluded from column $C_1$. Vessel C held water into which any vented oxygen flowed. At periodic intervals, the oxygen content of the water in vessels A and B was measured using an Orion $O_2$ electrode, model number 970800 and an Orion Digital Ionalzer Model Number 501. The electrode was recalibrated prior to each measurement.

As can be seen from Example 1, even at atmospheric pressure, from 26 to about 31 percent of the aqueous oxygen may be partitioned into the cyclohexane. Notably, this partitioning is achieved using only a relatively inefficient, unpacked column and a brief contact time. The use of a packed column or a baffled column would be expected to lead to increased transfer.

Figure 2:
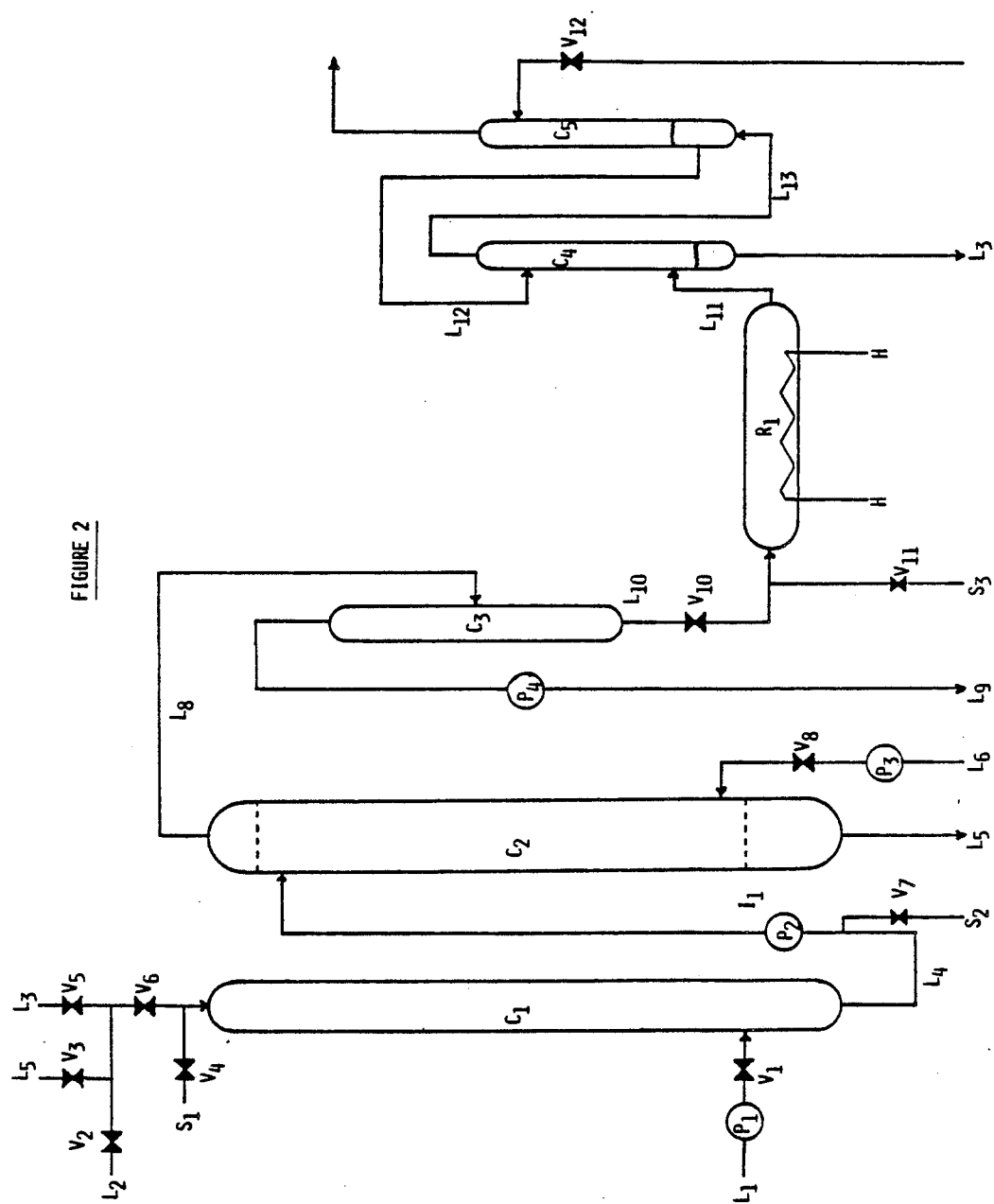
FIG. 2 represents a process for oxidizing a liquid hydrocarbon into oxygenated products which employs partitioning of oxidizing gas between an aqueous solution and the hydrocarbon to be oxidized. In addition.

FIG. 2 represents a process flow diagram for the large scale oxidation of a hydrocarbon, for example cyclohexane. The materials of construction are conventional and well known to those skilled in the art. Typically, stainless steels, clad or glass lined equipment is preferred in order to minimize corrosion. Due to the high pressures used, particularly in columns $C_1$ and $C_2$, a high aspect ratio is desirable for the process columns as the minimized diameter allows for economical use of construction material while providing a high safety margin. All columns, and reactor $R_1$ will generally be packed with traditional packing materials, e.g. balls, saddles, helices, etc., however tray columns and unpacked columns can, in theory, be used.

In operation, water is fed under pressure into the top of the oxygen solutioning column $C_1$ through valve $V_6$. The water may be fresh water from line $L_2$ via valve $V_2$ or may wholly or partially constitute recycle water as subsequently described. Oxygen in the form of pure oxygen, oxygen diluted with an gas inert under the process conditions, oxygen diluted with air, or atmospheric oxygen, is pressurized by pump $P_1$ and fed to column $C_1$ through valve $V_1$. Both the pressure and flow of oxygen may be adjusted to dissolve the desired mole percent oxygen in water.

Oxygen laden water exits the column through line $L_4$ and enters the partitioning column $C_2$ through pump $P_2$. Liquid hydrocarbon is pressurized in pump $P_3$ and fed to column $C_2$ via valve $V_8$. Due to the differences in specific gravity, a countercurrent flow situation is established, with the lighter, oxygen laden hydrocarbon exiting the column line $L_8$ while oxygen depleted water exits through line $L_5$ below the hydrocarbon/water interface $I_1$. In the case of hydrocarbons heavier than water, the entrance and exit points of the various streams will have to be reversed. In the case of hydrocarbons which are solid at ambient temperature, the columns will have to be heated to a temperature sufficient to maintain the hydrocarbon in the liquid phase.

From line $L_8$, the oxygen enriched hydrocarbon may enter a further partitioning column for further oxygen enrichment, or, as shown, may be degasified in column $C_3$. An important requirement of the process is that the system be maintained under pressure adequate to hold oxygen in solution without formation of a vapor phase. For this reason it is advisable to hold column $C_2$ at a slightly higher pressure than column C. Similarly, consideration must be given to pressure drops that occur in process lines. It is most desirable that no degasification due to pressure drop need occur, and therefore column $C_3$ is a redundant safety feature. Any recovered gas may be released to the atmosphere, flared, or preferably pressurized by pump $P_4$ and recycled to solutioning column $C_1$ through line $L_9$. Oxygen enriched hydrocarbon is metered into reactor $R_1$ through valve $V_{10}$. Reactor $R_1$ is operated at a suitable oxidizing temperature, for example from 100° C. to 200° C. Heat exchanger H is used to provide the heat required to initiate the reaction, and may supply additional heat or may remove heat from the reactor as the process demands.

The oxidation is generally promoted by the presence of a suitable catalyst in an amount of from about 0.01 to about 100 ppm. Due to the flexibility of the system, the catalyst may be added at one or more of several locations. It may be added, for example, to the water inlet of column $C_1$ via line $S_1$, and valve $V_4$ either as a water solution, or dissolved in a suitable solvent. Preferably, any solvent utilized will be one of the reaction products. When cyclohexane is oxidized, such a solvent might be cyclohexanol, cyclohexanone, or mixtures of these products. Alternatively, catalyst might be added prior to partitioning of oxygen from water to hydrocarbon by injection into line $L_4$ via line $S_2$ and valve $V_7$, or prior to oxidation, by injection via line $S_3$ and valve $V_{11}$ to line $L_{10}$.

The oxidized hydrocarbon stream generally contains from 1 to about 15 weight percent oxygenated products, more particularly about 3 to about 8 percent. Treatment of oxidized hydrocarbon may be accomplished in numerous ways. For example, the exit stream $L_{11}$ from $R_1$ might be reacted with caustic or by some other suitable method to decompose peroxides and hydroperoxides and then routed to column $C_4$. Alternatively, the oxidate might be fractionally distilled either prior or subsequent to peroxide and hydroperoxide decomposition. In the case of cyclohexane, for example, the higher boiling fraction containing cyclohexanone and cyclohexanol, both of which have some aqueous solubility, might be removed from the process at this point with the remainder, mostly cyclohexane, being routed to column $C_4$.

A further alternative is to bypass columns $C_4$ and $C_5$ entirely and process the $R_1$ effluent oxidate in the conventional manner. However it is an unusual additional feature of the subject invention, that any remaining, unreacted oxygen may be removed by "reverse partitioning" in column $C_4$ or, as shown, in columns $C_4$ and $C_5$, creating greater safety downstream from reactor $R_1$.

Fresh water may enter column $C_5$ through valve $V_{12}$, for example, exit through line $L_{12}$ into column $C_4$ and finally exit column $C_4$ through line $L_3$. Alternatively, fresh water might be added to both columns, in each case exiting through or near the bottom of the respective columns.

The water in line $L_3$ would then contain minor amounts of dissolved oxygen in addition to being saturated with hydrocarbon; dissolved oxygenated products; primarily mono- and di basic organic acids; and catalyst. This water may be recycled to column $C_1$ through valve $V_5$ where it might make up, for example, from 10 to 25 percent or more of total water in the system. Through proper balancing of the various fresh water inlet valves $V_2$ and $V_{12}$, the system should rapidly reach equilibrium with respect to the concentrations of the various system components in the aqueous streams. It might be necessary to periodically or continuously withdraw a portion of the aqueous streams, for example from lines $L_4$ or $L_5$ and rectify this take-off stream, routing deoxygenated, essentially hydrocarbon free water to column $C_4$ or $C_5$. Alternatively, the water used to remove unreacted oxygen could be de-gassed in column $C_6$ by reduction in pressure, then be treated as a source of dissolved organic acids through line $L_{14}$.

The embodiments of the invention in which an exclusive privilege or property is claimed are defined as follows:

1. In a process for the partial oxidation of hydrocarbons into an oxidate containing oxygenated hydrocarbon products, wherein molecular oxygen is used as the oxidizing agent, the improvement comprising the steps of:
   (a) preparing, in a separate vessel, an aqueous solution of oxygen;
   (b) contacting said aqueous oxygen solution with a liquid hydrocarbon to be oxidized in such a manner that a substantial quantity of oxygen is transferred from the aqueous phase to the hydrocarbon phase; and
   (c) thereafter oxidizing said oxygen-containing hydrocarbon at an elevated temperature.

2. The process of claim 1 wherein said aqueous solution is prepared by dissolving oxygen in water at a pressure of from about 5 bar to about 200 bar.

3. The process of claim 1 wherein said transfer of oxygen takes place in a column under conditions of countercurrent flow.

4. The process of claim 2 wherein said transfer of oxygen takes place in a column under conditions of countercurrent flow.

5. The process of claim 1 wherein the oxygen depleted water which is formed during step (b) is recycled to step (a).

6. The process of claim 2 wherein the oxygen depleted water which is formed during step (b) is recycled to step (a).

7. The process of claim 3 wherein the oxygen depleted water which is formed during step (b) is recycled to step (a).

8. The process of claim 4 wherein the oxygen depleted water which is formed during step (b) is recycled to step (a).

9. The process of claim 1 wherein step (b) takes place at ambient temperature.

10. The process of claim 4 wherein step (b) takes place at ambient temperature.

11. The process of claim 1 wherein step (b) takes place at a temperature greater than that of step (a).

12. In a process for the partial oxidation of hydrocarbons into an oxidate containing oxygenated hydrocarbon products, wherein molecular oxygen is used as the oxidizing agent, the improvement comprising the steps of:

a) preparing, in a separate vessel, an aqueous solution of oxygen;

b) contacting said aqueous oxygen solution with a liquid hydrocarbon to be oxidized in such a manner that a substantial quantity of oxygen is transferred from the aqueous phase to the hydrocarbon phase;

c) thereafter oxidizing said oxygen containing hydrocarbon at an elevated temperature; and d) removing any unreacted oxygen from the product of step (c) by means of counter current partitioning of oxygen between said product and water.

13. The process of claim 12 wherein said water in step (d) is fresh water.

14. The process of claim 12 wherein said water in step (d) is deoxygenated process water.

15. The process of claim 12 wherein the oxygen enriched water produced in step (d) is recycled to step (a).

16. The process of claim 13 wherein the oxygen enriched water produced in step (d) is recycled to step (a).

17. The process of claim 14 wherein the oxygen enriched water produced in step (d) is recycled to step (a).

18. The process of claim 12 wherein peroxides and hydroperoxides contained in the product of step (c) are decomposed prior to removing unreacted oxygen in step (d).

19. The process of claim 12 wherein peroxides and hydroperoxides contained in the product of step (c) are decomposed and the resulting mixture is fractionated into hydrocarbon and hydrocarbon oxidate fractions, with only the hydrocarbon fraction being treated in accordance with step (d).

* * * * *